United States Patent
Picetti et al.

(10) Patent No.: US 10,463,412 B2
(45) Date of Patent: Nov. 5, 2019

(54) MULTI-ROD BONE ATTACHMENT MEMBER

(71) Applicant: Warsaw Orthopedic, Inc, Warsaw, IN (US)

(72) Inventors: George D. Picetti, Sacramento, CA (US); Anthony J. Melkent, Germantown, TN (US); John Stewart Young, Olive Branch, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 15/483,824

(22) Filed: Apr. 10, 2017

(65) Prior Publication Data
US 2017/0209182 A1    Jul. 27, 2017

Related U.S. Application Data

(60) Continuation of application No. 14/096,370, filed on Dec. 4, 2013, now Pat. No. 9,615,867, which is a division of application No. 10/313,171, filed on Dec. 6, 2002, now abandoned.

(51) Int. Cl.
*A61B 17/70* (2006.01)
*A61B 17/86* (2006.01)

(52) U.S. Cl.
CPC ...... *A61B 17/8605* (2013.01); *A61B 17/7001* (2013.01); *A61B 17/7032* (2013.01); *A61B 17/7034* (2013.01); *A61B 17/7037* (2013.01); *A61B 17/7044* (2013.01)

(58) Field of Classification Search
CPC ............ A61B 17/7041; A61B 17/7046; A61B 17/7032; A61B 17/7035

USPC ................. 606/250–253, 264–275, 301–321
See application file for complete search history.

(56) References Cited

U.S. PATENT DOCUMENTS

| | | | |
|---|---|---|---|
| 4,805,602 A | 2/1989 | Puno et al. | |
| 4,946,458 A | 8/1990 | Harms et al. | |
| 5,005,562 A | 4/1991 | Cotrel | |
| 5,092,867 A | 3/1992 | Harms et al. | |
| 5,133,717 A * | 7/1992 | Chopin ............. | A61B 17/7055 606/264 |
| 5,176,680 A | 1/1993 | Vignaud et al. | |
| 5,207,676 A | 5/1993 | Canadell et al. | |
| 5,207,678 A | 5/1993 | Harms et al. | |
| 5,217,497 A | 6/1993 | Mehdian | |

(Continued)

FOREIGN PATENT DOCUMENTS

| | | |
|---|---|---|
| DE | 93 14 297 | 4/1994 |
| DE | 101 17 426 | 10/2002 |

(Continued)

OTHER PUBLICATIONS

Protest Under 37 C.F.R. Section 1.291, dated Mar. 3, 1997.

(Continued)

*Primary Examiner* — Matthew J Lawson

(57) ABSTRACT

A fixation element for use in orthopedic surgery, particularly spinal surgery is disclosed. The fixation element is capable of being screwed, hooked, or otherwise attached to a bone, and is configured to accommodate two or more rods or other elongated members. The head of the fixation elements thus has multiple places for positioning a rod, either vertically or horizontally spaced from each other.

20 Claims, 3 Drawing Sheets

(56) References Cited

U.S. PATENT DOCUMENTS

| | | |
|---|---|---|
| 5,261,909 A | 11/1993 | Sutterlin et al. |
| 5,261,912 A | 11/1993 | Frigg |
| 5,360,431 A | 11/1994 | Puno et al. |
| 5,443,467 A * | 8/1995 | Biedermann ...... A61B 17/7032 |
| | | 606/308 |
| 5,466,237 A | 11/1995 | Byrd et al. |
| 5,474,555 A | 12/1995 | Puno et al. |
| 5,476,464 A | 12/1995 | Metz-Stavenhagen et al. |
| 5,501,684 A | 3/1996 | Schlapfer et al. |
| 5,520,689 A | 5/1996 | Schlapfer et al. |
| 5,520,690 A | 5/1996 | Errico et al. |
| 5,531,746 A | 7/1996 | Errico et al. |
| 5,549,608 A | 8/1996 | Errico et al. |
| 5,554,157 A | 9/1996 | Errico et al. |
| 5,562,663 A * | 10/1996 | Wisnewski ........ A61B 17/7032 |
| | | 606/250 |
| 5,569,247 A | 10/1996 | Morrison |
| 5,575,792 A | 11/1996 | Errico et al. |
| 5,578,033 A | 11/1996 | Errico et al. |
| 5,584,833 A | 12/1996 | Fournet-Fayard et al. |
| 5,584,834 A | 12/1996 | Errico et al. |
| 5,586,984 A | 12/1996 | Errico et al. |
| 5,607,426 A | 3/1997 | Ralph et al. |
| 5,609,593 A | 3/1997 | Errico et al. |
| 5,609,594 A | 3/1997 | Errico et al. |
| 5,669,911 A | 9/1997 | Errico et al. |
| 5,672,176 A | 9/1997 | Biedermann et al. |
| 5,702,395 A | 12/1997 | Hopf |
| 5,993,449 A | 11/1999 | Schlapfer et al. |
| 6,706,044 B2 | 3/2004 | Kuslich et al. |
| 2002/0026193 A1 * | 2/2002 | Barker ............... A61B 17/7037 |
| | | 606/328 |
| 2002/0035365 A1 | 3/2002 | Kumar et al. |
| 2002/0138077 A1 * | 9/2002 | Ferree ............... A61B 17/7005 |
| | | 606/258 |
| 2003/0045874 A1 * | 3/2003 | Thomas, Jr. ....... A61B 17/7049 |
| | | 606/250 |
| 2003/0144664 A1 * | 7/2003 | Cavagna ............ A61B 17/701 |
| | | 606/265 |
| 2003/0216735 A1 * | 11/2003 | Altarac ............. A61B 17/7037 |
| | | 606/266 |
| 2004/0039388 A1 * | 2/2004 | Biedermann ...... A61B 17/6433 |
| | | 606/71 |

FOREIGN PATENT DOCUMENTS

| | | |
|---|---|---|
| EP | 0 242 708 | 4/1987 |
| FR | 2 734 471 A1 | 11/1996 |
| GB | 2 294 394 A | 1/1996 |
| WO | WO 95/32676 | 12/1995 |

OTHER PUBLICATIONS

Declaration of J.P. Errico Pursuant to Protest Under 37 C.F.R. Section 1.291, dated Mar. 3, 1997.
Sofamor Danek Meeting, May 2, 1996, entitled Implemedics.

* cited by examiner

MULTI-ROD BONE ATTACHMENT MEMBER

RELATED APPLICATIONS

This application is a Continuation of U.S. application Ser. No. 14/096,370 filed on Dec. 4, 2013, which is a Divisional of U.S. application Ser. No. 10/313,171, filed on Dec. 6, 2002, both of which are expressly incorporated herein by reference, in their entirety.

BACKGROUND OF THE INVENTION

A variety of implants are known in the art for attaching an elongated member, e.g. an elongated bar or rod, to one or more bones for the purpose of correcting deformity, promoting healing, or other therapeutic uses. Among such devices are those disclosed in U.S. Pat. No. 5,005,562 to Cotrel, U.S. Pat. No. 5,797,911 to Sherman et al., and U.S. Pat. No. 6,280,442 to Barker et al. In those devices, a U-shaped head is provided for accommodating an orthopedic rod, such as that used in corrective spinal surgery. A threaded element or hook connects the U-shaped head to a bone portion, and a set screw locks the elongated rod within the U-shaped head.

SUMMARY OF THE INVENTION

In one embodiment, an apparatus is disclosed which comprises a one-piece head portion having one or more channels, with the channels being configured so that a plurality of elongated members (e.g. spinal rods) may be connected to the head via one or more of the channels. At least one holder is connected to the head portion and holds at least one of the elongated members within their respective channels, and an attachment portion is provided connected to the head portion for connecting the head portion to a bone. There may be two substantially parallel channels in the head portion, with the head portion being substantially W-shaped. Such a pair of channels can have approximately the same width or radius, or one of the channels can have a width or radius larger than the other. A female thread can be formed in each of such channels, with set screws provided as the holders. The attachment portion may be integral with or may be movably connected with the head portion. If they are movably connected, the attachment portion may be rotatably or multi-axially connected with the head portion.

Another embodiment of an apparatus according to the invention comprises a head portion having first and second outer legs and at least one post between the legs, a first channel between the first leg and the post, and a second channel between the second leg and the post. A first thread is formed on the first leg and the post, and a second thread is formed on the second leg and the post. First and second set screws are provided, with the first set screw adapted to be threaded in the first thread to close the first channel, and the second set screw adapted to be threaded in the second thread to close the second channel. A bone connection portion is connected to the head portion, whereby the apparatus is connected to a bone. The apparatus can further comprise a first elongated member, such as a spinal rod, such that at least a portion of the first elongated member occupies at least a portion of the first channel. The first set screw provides a clamping force to hold the elongated member with respect to the head portion. A second elongated member can also be provided such that at least a portion of the second elongated member occupies at least a portion of the second channel in the head portion, and the second set screw provides a clamping force to hold the second elongated member with respect to the head portion.

A method is also disclosed, comprising providing a bone-engaging apparatus having an upper head portion and at least one lower attachment portion, with the head portion having a plurality of channels for receiving one or more elongated members; connecting the attachment portion of the apparatus to a bone; inserting an elongated member into one of the channels; and connecting a holder to said head portion to hold said elongated member in said channel. The holder connecting step can include threading a set screw into the channel into which the elongated member has been inserted until the set screw exerts a clamping force on said elongated member sufficient to lock it with respect to the head portion. The method may further include inserting a second elongated member into one of the channels. The channel into which the second elongated member is inserted can be previously occupied or unoccupied by an elongated member. An additional holder may be provided, if necessary, for the second elongated member. For example, a set screw may be threaded into the channel into which the second elongated member has been inserted until it exerts a clamping force on the second elongated member. The method may also include adjusting the bone prior to insertion of the first elongated member, and further adjustment of the bone prior to insertion of the second elongated member. The relative position of the attachment portion and the head portion may be adjusted prior to a time when the elongated member(s) are locked with respect to the apparatus.

DESCRIPTION OF THE PREFERRED EMBODIMENT

Figure 3:
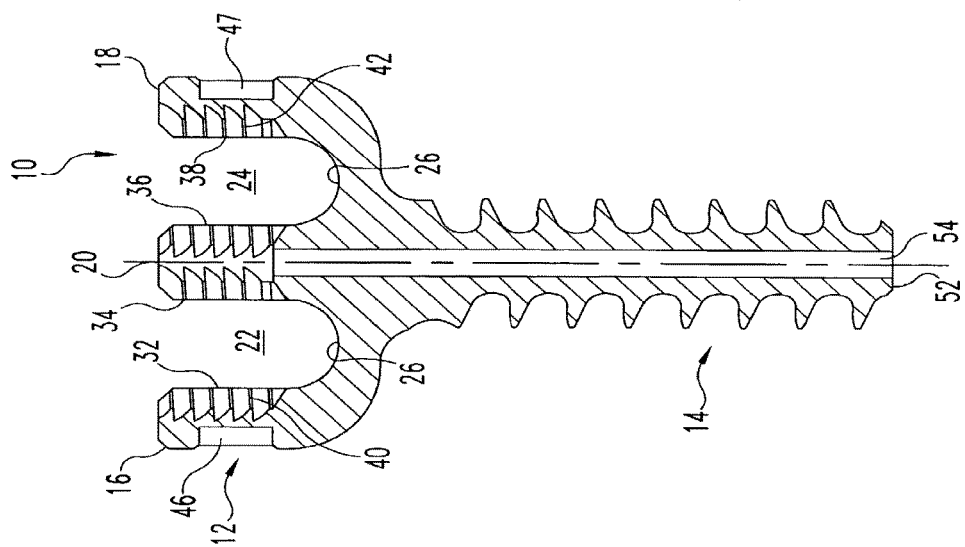
FIG. 3 is a cross-sectional view taken along the lines 3-3 and viewed in the direction of the arrows of the embodiment shown in FIG. 1.
Figure 2:
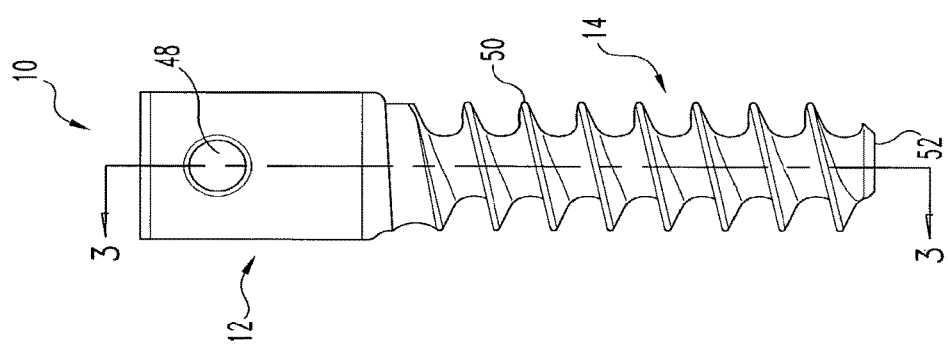
FIG. 2 is a side view of the embodiment shown in FIG. 1.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated, as would normally occur to one skilled in the art to which the invention relates.

Figure 1:
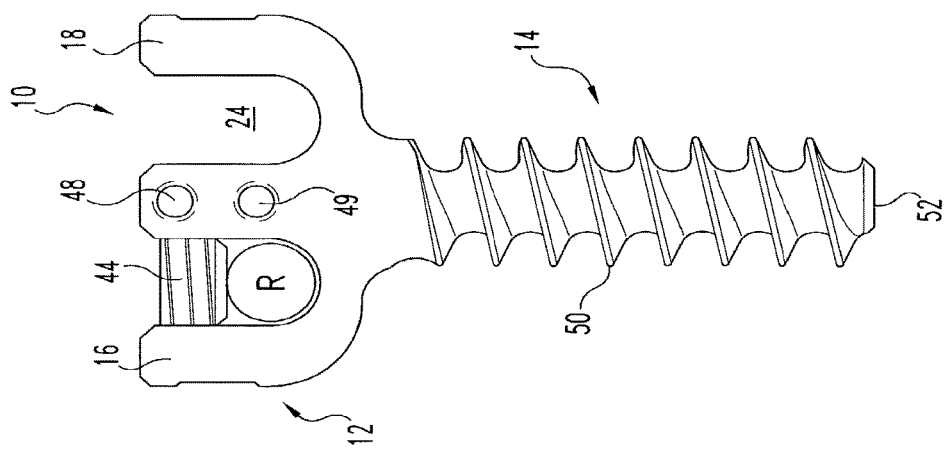
FIG. 1 is a front elevational view of a first embodiment of a bone fixation element according to the invention.

Referring now generally to FIG. 1, there is shown one embodiment of a fixation element 10 according to the present invention. In that embodiment, fixation element 10 includes a head portion 12 and an attachment portion 14. Although fixation element 10 is depicted as a bone screw, with a threaded attachment portion 14, one of ordinary skill in this art will appreciate that threaded attachment portion 14 could be replaced with a U-shaped or L-shaped hook element adapted to be fixed to a part of a bone, such as a pedicle or spinous process of a vertebra, or with another device allowing connection to a bone.

In the embodiment shown in FIG. 1, head portion 12 is substantially in the shape of a W, having two outer legs or legs 16, 18, and a post 20 between legs 16, 18. Leg 16 and post 20 form a first channel 22, and leg 18 and post 20 form a second channel 24. Channels 22 and 24 are preferably substantially straight and substantially parallel, and have a lower surface 26, 28, which may be curved or form a part of a cylinder. Channels 22 and 24 are sized and shaped to accommodate a rod or other elongated element R. In one particular embodiment, channels 22 and 24 are sized to accommodate rods of the same size, as for example where the radius of curvature of surfaces 26 and 28 are equal.

Channels 22 and 24 are bounded by wall sections 32 and 34, and 36 and 38, respectively. Wall section 32 is an inner part of leg 16, wall sections 34 and 36 form sides of post 20, and wall section 38 is an inner part of leg 18. Wall sections 32 and 34 include a female thread 40, and wall sections 36 and 38 include a female thread 42. Threads 40 and 42 are adapted to accommodate set screws, such as that denoted as 44 in FIG. 1, and threads 40, 42 and set screws 44 are holders that close channel 22 and hold or lock a rod or other elongated member therein. The size of the set screw needed to close channel 22 will, of course, depend on the characteristics of thread 40, just as thread 42 will determine the size of the set screw for channel 24. If an alternative holder is desired (such as a cam lock, a sliding member, a cap or nut with threads or a bayonet-lock), threads 40 and/or 42 may be altered, removed, or replaced with other features (e.g. grooves, external threads or the like) that permit connection to such holders.

Further, in the above-described embodiment it is preferred that there be a set screw 44 and compatible threads (e.g. threads 40, 42) for each channel, i.e. a first set screw 44 for channel 22 and a second set screw 44 for channel 24. It would be possible to use one or more holders of another type, e.g. caps or nuts, to contain or lock multiple rods or other elongated members within their specific channels. For example, a cap or nut that surrounded and connected to legs 16 and 18 of head portion 12 would close both channels 22 and 24 and keep elongated member(s) therein. In that case, there would be one holder to hold one or more elongated members within their respective channels, whereas with set screws several holders (i.e. set screws) may be needed to hold several elongated members within their respective channels. It will also be observed that not all holders elements need be the same, but that screws, nuts, caps, sliders or cams can be combined for use with a given head portion.

In the embodiment of fixation member 10 in which channels 22 and 24 accommodate rods of the same size, the widths of the channels (i.e. the respective distances between walls 32 and 34 and between walls 36 and 38) will be approximately equal, and may accommodate identical set screws. On the outsides of legs 16 and 18 are found indentations 46 and 48, respectively. Indentations 46 and 48 are adapted to accommodate a holding or twisting tool, such as a screwdriver. In one embodiment, indentations 46 and 48 are substantially circular, and may have a slightly tapered opening, so that a projection on a gripping or screwing tool that has a circular or other shape can easily be inserted into indentations 46 and 48.

In the embodiment of FIG. 1, attachment portion 14 may be formed integrally with head portion 12, or may be made separately from head portion 12 and fixedly attached to head portion 12 after manufacture. Attachment portion 14 is a threaded member in the illustrated embodiment, having threads 50 adapted for insertion into a bone. Attachment portion 14 is illustrated as having a flattened end 52, but it will be understood that end 52 may also be pointed and/or self-tapping. Fixation element 10 may also be cannulated, i.e. having an aperture 54 extending from end 52 of attachment portion 14 to the top of post 20 of head portion 12. The embodiment of FIG. 1 also shows attachment portion 14 along a medial axis (i.e. equidistant from the outside edges of legs 16 and 18) of head portion 12. As shown and described below with respect to other embodiments, attachment portion 14 may be placed to one side of a medial axis, for example directly beneath one of channels 22 and 24.

In use, access to an orthopedic surgical site is obtained in a known manner. A drill or similar device is used to make a hole in a bone. For convenience, use of fixation element 10 will be described with respect to spinal surgery, although it is understood that the present invention may be used with other bony tissue or another surgical site. After a hole is drilled in a vertebra, attachment portion 14 of fixation element 10 is inserted, and fixation element 10 is rotated so that fixation element 10 is screwed into the hole. The surgeon continues turning fixation element 10 until it is in a desired position, e.g. head portion 12 is at a desired height from the surface of the vertebra, and channels 22 and 24 are oriented as the surgeon desires for a rod. When used in spinal surgery, commonly fixation element 10 will be threaded into the bone until most or all of thread 50 is within the bone, and channels 22 and 24 are oriented substantially along the spinal column or along a desired orientation of one or more spinal segments.

One or more rods or other elongated members can then be connected to fixation element 10. As shown in FIG. 1, rod R is placed in channel 22, and set screw 44 is screwed into internal thread 40 to close channel 22 and hold or lock rod R therein. Of course, rod R may also be placed in channel 24, in substantially the same manner as described above. If two rods are used, one rod may be placed in each of channels 22 and 24 and held or locked therein with set screws, as described above.

In a minimally-invasive procedure, access to the surgical site is available through one or more small openings through the skin and/or other soft tissues. Instruments suited to minimally-invasive procedures are inserted through such an opening and moved to the surgical site, where the steps described above are performed. Although this invention can be used in a variety of surgical techniques, it has been found to have significant application in minimally-invasive spinal surgery. In such procedures, it can be difficult to use screws or hooks that accommodate only a single rod or other elongated member, because of the rigidity of the corrective rod that must be implanted and because of the relative lack of mechanical advantage to adjust the spine when it is not exposed. Using the present invention, a surgeon can insert a screw or hook minimally-invasively, perform a degree of adjustment to the spine and connect a first rod that may be somewhat less rigid than is normally used in corrective spinal surgery (e.g. scoliosis-correcting surgery). The first rod holds the affected spinal segment(s) sufficiently while another, more-rigid rod is prepared and the spine adjusted to its final, corrected position. The second rod is then inserted and locked into the screws or hooks, and the surgery is completed. In some cases, it is contemplated that use of yet additional rods or other elongated members or additional spine-adjustment steps may be indicated or necessary, and thus screws or hooks that accommodate three or more rods come within the spirit of the invention.

Several other embodiments are described below. For convenience, features or aspects that are identical or similar in two or more embodiments disclosed herein are denoted in the description and drawings by numbers sharing their last two digits.

Figure 4:
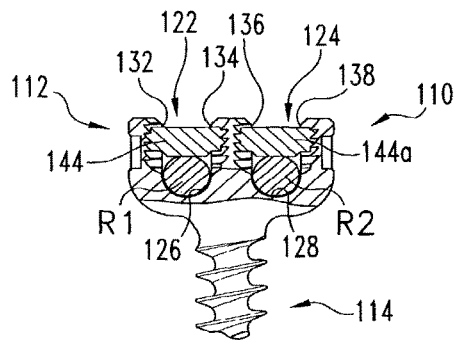
FIG. 4 is a partial cross-sectional view of a further embodiment of a bone fixation element according to the invention.

An alternative embodiment of a fixation member 110 is depicted in FIG. 4. Fixation element 110 is substantially the same as fixation member 10 with the exception that fixation member 110 has one channel (e.g. channel 124) that will accommodate a rod larger than the other (e.g. channel 122) will accommodate. Lower surface 126 of channel 122 has a smaller radius than bottom surface 128 of channel 124, and the distance between walls 132 and 134 of channel 122 is smaller than the distance between walls 136 and 138 of channel 124. A smaller set screw or other holding or locking element may be used in channel 122 compared to that used in channel 124. In other respects, fixation element 110 is essentially the same as fixation element 10.

Fixation element 110 may be used where it is preferred to have two rods of different diameters in a particular orthopedic construct. In the spinal surgical field, for example, it is common to reposition (distract, compress, rotate, or otherwise adjust relative location) vertebrae prior to or during implantation of a supporting or corrective apparatus. Connecting a smaller, less-rigid rod to fixation element 110 as described above will allow some holding or support of a spine that has been adjusted, while still allowing the surgeon to readjust the spine and/or contour a larger, more-rigid rod for providing the main support or correction to the spine.

Fixation element 110 may be placed in a vertebra as described above with respect to fixation element 10. A first rod R1 of relatively smaller diameter may be placed in channel 122, and held with a set screw 144. The surgeon can then perform additional or new repositioning procedures if he or she chooses, and may bend the locked rod in the process. While the relatively smaller rod R1 is holding the vertebra as desired, the surgeon can contour a larger rod R2 or perform other surgical procedures while the spine is held by the relatively smaller rod. The relatively larger rod R2, once prepared as the surgeon desires, can then be inserted into channel 124 of fixation element 110, and locked with another set screw 144a.

It will be noted that in the illustrated embodiments of fixation elements 10 and 110, the attachment portion 14, 114 is substantially centered between legs 16 and 18. The present invention includes embodiments in which attachment portion 14 may be nearer to one leg or another, or it may be directly beneath one of channels 22 or 24, or have some other non-symmetrical configuration.

Figure 5:
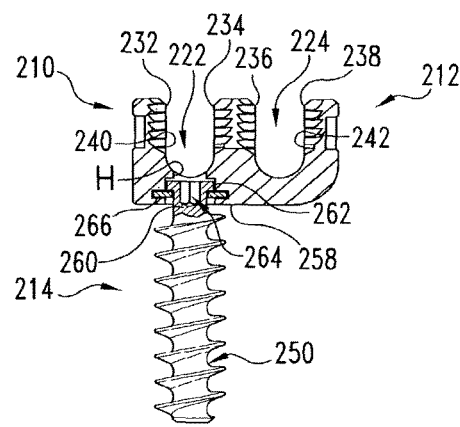
FIG. 5 is a partial cross-sectional view of another embodiment of a bone fixation element according to the invention.

Turning now to FIG. 5, there is shown a fixation element 210. Fixation element 210 is similar to fixation element 10, except head portion 212 and attachment portion 214 are not initially integral with or fixed to each other. Rather, attachment portion 214 is separate from head portion 212, and is rotatable with respect to head portion 212. Like fixation element 10, fixation element 210 includes head portion 212 having two channels 222 and 224. The channels have wall sections 232, 234, 236 and 238 that are threaded with threads 240, 242. One of the channels, e.g. channel 222, communicates with a hole H that extends from the top to the bottom of head portion 212. Toward the bottom end of head portion 212, a groove 258 is set, essentially surrounding hole H.

Attachment portion 214 in this embodiment is a bone screw having bone threads 250 and a head 260, although it will be understood that hook could be provided on attachment portion 214 instead. Head 260 is substantially cylindrical, with a flange 262 at the top of head 260, and an internal print 264 within head 260 to enable attachment portion 214 to be screwed into a bone.

Fixation element 210 is assembled by inserting head 260 of attachment portion 214 into hole H of head portion 212 through the bottom end of head portion 212. A C-shaped snap ring 266 is provided to retain attachment portion 214 within head portion 212. Snap ring 266 has an inner diameter larger than the diameter of head 260, but smaller than the diameter of flange 262 of head 260. The outer diameter of snap ring 266, in its non-stressed state, is slightly larger than the diameter of groove 258 in head portion 212. Thus, attachment portion 214 is rotatable with respect to head portion 212, but not necessarily multi-axially moveable with respect to head portion 212.

To use fixation element 210, a hole in a bone (e.g. a vertebra) is prepared as described above. The assembled fixation element 210 is then coupled to the bone, by inserting the attachment portion 214 into the hole and screwing it into the bone. Attachment portion 214 may be screwed in to a point where the bottom of head portion 212 contacts bone and flange 262 presses against snap-ring 266, effectively holding attachment portion 214 with respect to head portion 212. Alternatively, attachment portion 214 can be screwed in to a lesser degree, with rotation of head portion 212 with respect to attachment portion 214 being inhibited or prevented by insertion of one or more rods into one or both channels 222, 224. Once such rod(s) are inserted into one or both of channels 222 and 224 they are locked therein, as described above with respect to fixation element 10.

Figure 6:
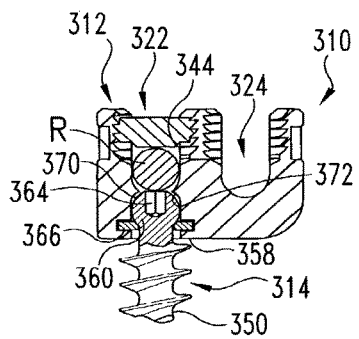
FIG. 6 is a partial cross-sectional view of yet another embodiment of a bone fixation element according to the invention.

Referring now to FIG. 6, there is shown an embodiment of a fixation element 310. Fixation element 310 is very similar to fixation element 210, except that attachment portion 314 is configured so that its connection with head portion 312 is a multi-axial connection. A preferred configuration for the connection between head portion 312 and attachment portion 314 is disclosed in U.S. Pat. No. 6,280,445 to Barker et al., the entirety of which is incorporated by reference. Accordingly, attachment portion 314 includes a rounded head 360 that sits within hole H of head portion 312, and is retained therein by a C-shaped snap ring 366 seated in groove 358. A crown member 370 sets atop the head 360 of attachment portion 314.

Fixation element 310 is connected to a bone in essentially the same fashion as fixation element 210 described above. After attachment portion 314 is screwed into the bone, head portion 312 may be adjusted multi-axially with respect to attachment portion 314. A rod is introduced into channel 322, and any further multi-axial adjustments of head portion 312 with respect to attachment portion 314 can be made. A set screw 344 is threaded into threads 340 communicating with channel 322. Locking down set screw 344 presses the rod down on crown member 370, which locks head 360 of attachment portion 314 between crown member 370 and snap ring 362. In a particular embodiment, head 360 may have ridges 372 that are somewhat harder than the material of crown member 370, so that crown member 370 and head 360 are locked together by ridges 372 biting into crown member 370.

Figure 7:
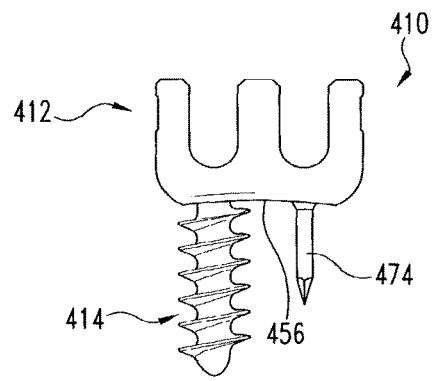
FIG. 7 is a partial cross-sectional view of another embodiment of a bone fixation element according to the invention.

Referring now to FIG. 7, a further embodiment of a fixation element 410 is disclosed. Fixation element 410 includes a head portion 412 and an attachment portion 414. In fixation element 410, head portion 412 and attachment portion 414 may be integral or initially fixed with each other (as in fixation member 10), rotatable with respect to each other (as in fixation member 210), or multi-axially connected (as in fixation member 310). Head portion 412 includes an underside 456 having an approximately anatomically-shaped curvature. In a specific embodiment, the curvature has a concave aspect that approximates the curvature of a side of a vertebra. In another embodiment, the curvature may have a concave aspect in a first cross-section and a convex aspect in a second cross-section, e.g. one perpendicular to the first cross-section. Extending from surface 456 is a prong or spike 474. Spike 474 is intended to be inserted into the bone tissue when fixation element 410 is attached to a bone, to provide yet further stability to the implant construct. In other respects, fixation element 410 can have any of the features or attributes of fixation elements 10, 110, 210, and/or 310.

Figure 8:
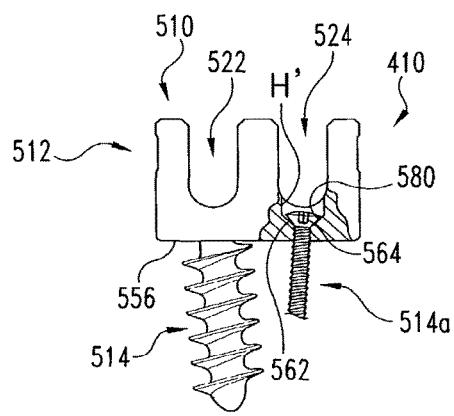
FIG. 8 is a partial cross-sectional view of a still further embodiment of a bone fixation element according to the invention.

Referring now to FIG. 8, fixation element 510 in yet another embodiment is disclosed. Fixation element 510 may include attributes or features from any of fixation elements 10, 110, 210, and/or 310, wherein an attachment portion 514 is not centered with respect to head portion 512, or is beneath one channel (e.g. channel 522) of head portion 512. In addition, fixation element 510 includes a second attachment portion 514a connected to head portion 512. In a specific embodiment, head portion 512 can include a hole H' communicating with channel 524 and extending from bottom surface 556 through head portion 512. Attachment portion 514a can be similar to attachment portion 214 or 314, in which case the features of fixation elements 210 and/or 310 providing for connection between the respective attachment portions and head portions would be included in fixation element 510. Alternatively, attachment portion 514a may be a standard bone screw with a curvate head 562 and an internal print 564, that could rest against the lower edge of the hole H'. In that case, an additional hole 580 may be provided that communicates with hole H', and is threaded to accommodate a set screw (not shown) therein, which can lock attachment portion 514a within hole H' in a desired orientation.

Fixation element 510 is attached to a bone in substantially the same fashion as described above, except an additional hole must be drilled in a bone to accommodate attachment portion 514a. As one example, attachment portion 514 can be threaded into the bone, and attachment portion 514a can then be threaded into the second hole in the bone and used to make adjustments in the positioning of fixation element 510 with respect to the bone. One or more rods may be inserted in channels 522 and 524, and fixation element 510 locked with respect to the rods by threading set screws down on them, as described above.

Figure 9:
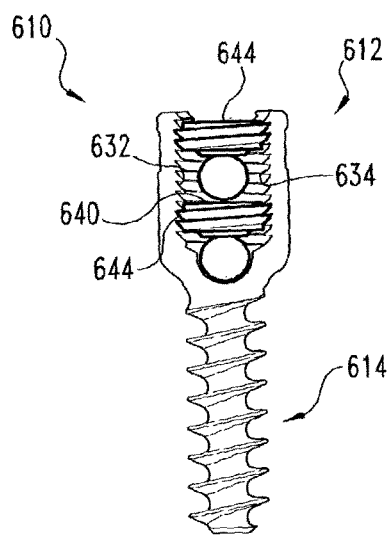
FIG. 9 is a partial cross-sectional view of another embodiment of a bone fixation element according to the invention.

Referring now to FIG. 9, there is shown an embodiment 610 of a fixation element. Fixation element 610 has a U-shaped head portion 612 with a single channel 622 therethrough, and is connected to an attachment portion 614 which in a specific embodiment is a threaded screw portion. Walls 632 and 634 of channel 622 include threads 640 for accommodating a set screw 644. Walls 632 and 634 are of a height that enables insertion of two separate rods within channel 622 of head portion 612. Thus, for a fixation element 610 intended to accommodate two rods of 5.5 mm diameter, the height of walls 632 and 634 would be at least 11 mm plus the height of set screw(s) 644. With reference to FIG. 9, rod R1 is placed within channel 622, followed by a set screw 644, screwed into thread 640. A second rod R2 would be placed atop set screw 644, and a second set screw 644 would be threaded into threads 640 to lock the second rod R2 with respect to head portion 612.

The diameters of rods R1 and R2 could be equal or they may be different to provide adjustability and stability prior to final locking down as described above. It will also be noted that a configuration of head portion 612 to accommodate two rods may be combined with a multi-axial head portion/attachment portion connection (such as those shown in U.S. Pat. No. 5,797,911 to Sherman et al. and U.S. Pat. No. 6,280,445 to Barker et al., the entireties of which are incorporated herein by reference), or could be rotational with respect to each other as shown above with respect to fixation member 210. Further, although channel 622 is shown as extending from a back or proximal surface of head portion 612 toward attachment portion 614, it will be understood that channel 622 could extend laterally, i.e. from a side surface of head portion 612 toward an opposite side surface. Two rods or other elongated members could then be inserted into channel 622 from the side and fixed with respect to head portion 612 substantially as described above, or as described further below with respect to FIGS. 10 and 11.

Figure 10:
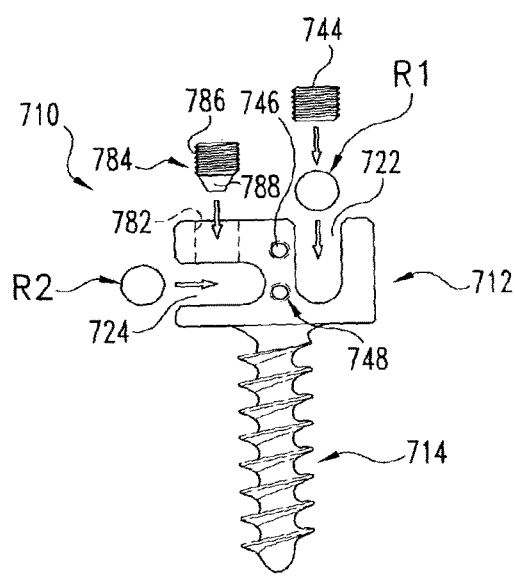
FIG. 10 is a side view of yet another embodiment of a bone fixation element according to the invention.

Yet a further embodiment is shown in FIG. 10. A fixation element 710 is provided with a head portion 712 and an attachment portion 714. In this embodiment, head portion 712 has channels 722 and 724. Channel 722, like channel 22 in FIG. 1, is substantially straight, extends through head portion 712, and is open to the back (i.e. the portion opposite attachment portion 714) of head portion 712. Channel 724 is also substantially straight and extends through head portion 712, but channel 724 opens to the side of head portion 712. Thus, head portion 712 has one channel that is "back-loading" for one elongated member (e.g. rod R1 in FIG. 4 or 9) and "side-loading" for another elongated member (e.g. rod R2 in FIG. 4 or 9).

Head portion 712 may also include a hole 782 from the back of head portion 712 to channel 724. Hole 782 may be internally threaded and accommodate a set screw 784, which is used to lock a rod within channel 724. In one embodiment, set screw 784 has a threaded portion 786, and may also have a conically-shaped or tapered end portion 788. It will be understood that any of several types of holder or locking member, including a set screw 744 (threaded into hole 782 or into channel 724 from the side of head portion 712) or other holder(s) described above, can be used. Channel 722 is configured to accommodate a holder such as set screw 744 or other holder(s) described above.

Head portion 712 is shown in this embodiment to be fixed with respect to attachment portion 714, with attachment portion 714 substantially in the middle of head portion 712. Of course, attachment portion 714 may be rotatably or multi-axially connected to head portion 712, or located toward one side of head portion 712, or multiple attachment portions 714 may be provided, as described in detail above.

Figure 11:
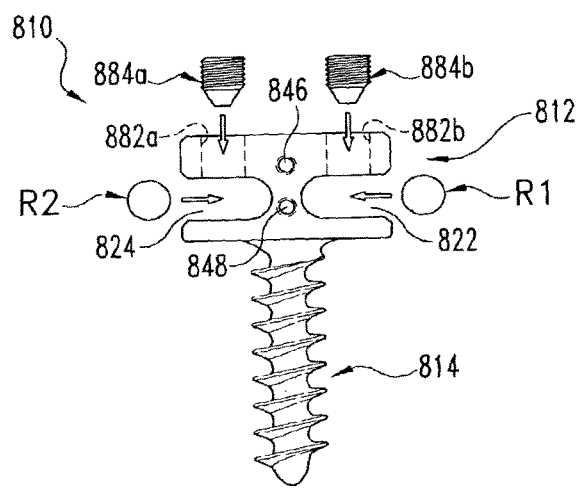
FIG. 11 is a side view of another embodiment of a bone fixation element according to the invention.

Another embodiment of a fixation element 810 is shown in FIG. 11. Fixation element 810 is much like fixation element 710, with the exception that both channels 822 and 824 are open to the sides of head portion 812 of fixation element 810. In one particular embodiment, holes 882a and 882b are provided to communicated with channels 822 and 824. Holes 882a and 882b may be internally threaded (as described above) to accommodate set screws such as 884a and 884b, or may be configured to accommodate alternative holders, as described above. As with fixation element 710, attachment portion 814 of fixation element 810 may be rotatably or multi-axially connected to head portion 812, or located toward one side of head portion 812, or multiple attachment portions 814 may be provided, as described in detail above.

The implants described above are preferably made from a biocompatible material such as stainless steel, titanium, plastics or other sturdy biocompatible and/or resorbable materials. The elongated members may be flexible or rigid rods, cables or similar items. It is envisioned that well-known open and minimally-invasive surgical procedures may be used to implant embodiments of the present invention.

The size of the implants described above may be identical or similar to implants currently used in spinal and other orthopedic surgeries. It has been found that the implants described above may have particular application to smaller vertebrae or other bones (e.g. those in children or other small persons, or adult cervical vertebrae), since one implant attaching to a bone can accommodate two rods or other elongated members. Accordingly, these implants may be made in standard and smaller sizes for such uses.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. For example, while the embodiments described above have two channels (e.g. channels 22 and 24) for accommodating longitudinal supports, the present invention contemplates fixation elements with head portions having a larger number of channels or that can accommodate more than two rods or other support members. Further, it will be seen that aspects of one embodiment described above can be incorporated into another of the embodiments. For example, the "stacked rod" feature of fixation element 610 could be included with fixation element 10. In that case, one of the channels of fixation element 10 would be of a height sufficient to place one rod atop another in that channel, as described with respect to fixation element 610. Still further, it will be seen that the channel or channels may be differently oriented, as for example opening to the side of the head portion.

What is claimed is:

1. A fastening system comprising:
   a. a first head portion comprising opposite top and bottom surfaces, a first channel and a second channel that is spaced apart from the first channel, the first and second channels extending through the top surface, the first head portion defining an axis extending from said first channel to said second channel, said first and second channel extending perpendicular to said axis, the head portion comprising an inner surface defining a hole that extends through the bottom surface;
   b. a first attachment portion comprising a bone-engaging portion and a head configured such that the first head portion is rotatable relative to the attachment portion in a plurality of planes when the first attachment portion is disposed in the hole in the first head portion;
   c. a second head portion comprising a first channel and a second channel comprising an inner surface defining a hole;
   d. a second attachment portion comprising a bone-engaging portion and a head configured such that the second head portion is rotatable relative to the attachment portion in a plurality of planes when the second attachment portion is disposed in the hole of the second head portion;
   e. a first cylindrical rod;
   f. a second cylindrical rod,
   wherein at least one of the channels has a depth extending parallel to the hole that is greater than a thickness of at least one of the rods, and
   wherein the first head portion and second head portion are configured to be connected via the first cylindrical rod and the second cylindrical rod when the first rod is positioned in the first channel of the first head portion and the second head portion and the second rod is positioned in the second channel of the first head portion and the second head portion.

2. The fastening system of claim 1, wherein each of the first and second head portions comprises a first leg, a second leg and a third leg positioned between the first and second legs, the first leg and a first surface of the third leg defining the first channel, the second leg and a second surface of the third leg defining the second channel, wherein the first leg and the first surface comprise threads that face one another and the second leg and the second surface comprise threads that face one another.

3. The fastening system of claim 1, further comprising two crown members comprising a concave surface that engages a convex surface of each head of the first and second attachment portions, wherein the first crown member is positioned between the inner surface of the first head portion that defines the hole and the head of the first attachment portion, and the second crown member is positioned between the inner surface of the second head portion that defines the hole and the head of the second attachment portion.

4. The fastening system of claim 1, further comprising two rings, wherein the first ring is positioned between the bone-engaging portion and the head of the first attachment portion, and the second ring is positioned between the bone-engaging portion and the head of the second attachment portion.

5. The fastening system of claim 1, further comprising:
   a. two crown members comprising a concave surface that engages a convex surface of each head of the first and second attachment portions, wherein the first crown member is positioned between the inner surface of the first head portion that defines the hole and the head of the first attachment portion, and the second crown member is positioned between the inner surface of the second head portion that defines the hole and the head of the second attachment portion; and
   b. two rings, wherein the first ring is positioned between the bone-engaging portion and the head of the first attachment portion, and the second ring is positioned between the bone-engaging portion and the head of the second attachment portion.

6. The fastening system of claim 1, further comprising:
   a. a first set screw configured to threadingly engage the first channel in the first head portion such that an end surface of the first set screw engages the first cylindrical rod;

b. a second set screw configured to threadingly engage the second channel in the first head portion such that an end surface of the second set screw engages the second cylindrical rod;
c. a third set screw configured to threadingly engage the first channel in the second head portion such that an end surface of the third set screw engages the first cylindrical rod; and
d. a fourth set screw configured to threadingly engage the second channel of the second head portion such that an end surface of the fourth set screw engages the second cylindrical rod.

7. The fastening system of claim 1, wherein the head of the first attachment portion further comprises ridges.

8. The fastening system of claim 1, wherein the second head portion comprises opposite top and bottom surfaces, the first and second channels of the second head portion extending through the top surface of the second head portion, the hole of the second head portion extending through the bottom surface of the second head portion.

9. The fastening system of claim 1, wherein the hole of the first head portion extending is in communication with the first channel of the first head portion.

10. The fastening system of claim 1, wherein the first and second channels of the first head portion are spaced apart from one another by a wall, the wall including a first side that defines a portion of the first channel of the first head portion and a second side that defines a portion of the second channel of the first head portion, the sides being threaded.

11. The fastening system of claim 1, further comprising a crown that directly engages the head of the first attachment portion and the first cylindrical rod.

12. A fastening system comprising:
a first head portion comprising a first leg, a second leg and a post between the legs, the first leg and the post defining a first U-shaped channel, the second leg and the post defining a second U-shaped channel that extends parallel to the first channel, the first head portion comprising a hole positioned between the first leg and the post;
a first attachment portion comprising a bone-engaging portion and a head configured such that the first head portion is rotatable relative to the first attachment portion in a plurality of planes when the first attachment portion is disposed in the hole in the first head portion;
a second head portion comprising a first channel, a second channel and an inner surface defining a hole;
a second attachment portion comprising a bone-engaging portion and a head configured such that the second head portion is rotatable relative to the second attachment portion in a plurality of planes when the second attachment portion is disposed in the hole of the second head portion;
a first rod positioned in the first channels; and
a second rod positioned in the second channels,
wherein at least one of the channels has a depth extending parallel to the hole that is greater than a thickness of at least one of the rods extending parallel to the hole that is.

13. The fastening system of claim 12, wherein the first head portion comprises opposite top and bottom surfaces, the channels of the first head portion extending through the top surface, the hole of the first head portion extending through the bottom surface.

14. The fastening system of claim 12, wherein the first channels each include an opening having a diameter that is greater than a diameter of the first rod and the second channels each include an opening having a diameter that is greater than a diameter of the second rod.

15. The fastening system of claim 12, wherein an inner surface of the first leg and a surface of the post comprise threads configured for engagement with a set screw, the fastening system further comprising the set screw, wherein the set screw engages the threads on the inner surface of the first leg, the threads on the surface of the post and the first rod.

16. The fastening system of claim 15, wherein an inner surface of the second leg and a second surface of the post comprise threads configured for engagement with a second set screw.

17. The fastening system of claim 12, wherein the first head portion comprises a groove that is in communication with the hole of the first head portion, the fastening system comprising a ring that is disposed in the groove and engages the head of the first attachment portion to retain the head of the first attachment portion within the hole of the first head portion.

18. The fastening system of claim 12, wherein the hole of the first head portion is in communication with the first channel of the first head portion.

19. The fastening system of claim 12, wherein the channels of the first head portion extend through the top surface without extending through the bottom surface.

20. The fastening system of claim 12, wherein the first leg comprises a first cavity that extends into an outer surface of the first leg without extending through an opposite inner surface of the first leg, the second leg comprising a second cavity opposite the first cavity that extends into an outer surface of the second leg without extending through an inner surface of the second leg.

* * * * *